United States Patent

Dickson et al.

Patent Number: 6,117,317
Date of Patent: Sep. 12, 2000

[54] CHROMATOGRAPHIC COLUMN AND VALVE WITH MOVABLE VALVE SLEEVE

[75] Inventors: Nicola Jane Dickson, North Nibley; Neil Frazer, Stroud, both of United Kingdom

[73] Assignee: Millipore Investment Holdings Limited, Wilmington, Del.

[21] Appl. No.: 08/862,536

[22] Filed: May 23, 1997

[51] Int. Cl.⁷ .................................................. B01D 15/08
[52] U.S. Cl. ................................................... 210/198.2
[58] Field of Search .......................... 210/656, 198.2; 73/23.22, 23.35, 61.55, 61.53; 95/82; 137/625.25, 625.14, 625.17, 625.67, 625.68

[56] References Cited

U.S. PATENT DOCUMENTS

| | | | |
|---|---|---|---|
| 402,224 | 4/1889 | Belssing . | |
| 691,975 | 1/1902 | Schaaf . | |
| 1,481,651 | 1/1924 | Nixon . | |
| 2,236,210 | 3/1941 | Foggan | 417/554 |
| 2,941,821 | 6/1960 | Klee | 137/343 |
| 2,997,055 | 8/1961 | Cadonau et al. | 137/240 |
| 3,522,824 | 8/1970 | Allen et al. | 141/90 |
| 3,874,825 | 4/1975 | Jentsch | 417/519 |
| 4,015,631 | 4/1977 | Hayes | 137/625.33 |
| 4,079,009 | 3/1978 | Seller et al. | 210/198.2 |
| 4,245,760 | 1/1981 | Stevenson et al. | 222/148 |
| 4,249,560 | 2/1981 | Raque et al. | 137/240 |
| 4,252,021 | 2/1981 | Drushel | 73/863.72 |
| 4,325,401 | 4/1982 | Ukai et al. | 137/240 |
| 4,336,772 | 6/1982 | Schweitzer | 123/25 |
| 4,344,453 | 8/1982 | Tuchenhagen et al. | 137/240 |
| 4,436,106 | 3/1984 | Tuchenhagen et al. | 137/240 |
| 4,444,066 | 4/1984 | Ogle et al. | 73/863.72 |
| 4,458,543 | 7/1984 | Mieth | 73/863.86 |
| 4,513,780 | 4/1985 | Evans . | |
| 4,582,204 | 4/1986 | Wright | 211/133.1 |
| 4,757,834 | 7/1988 | Mieth | 137/15.06 |
| 4,827,967 | 5/1989 | Junier | 137/240 |
| 4,891,133 | 1/1990 | Colvin, Jr. | 210/198.2 |
| 4,894,152 | 1/1990 | Colvin, Jr. et al. | 210/198.2 |
| 4,896,545 | 1/1990 | Averette | 73/863.01 |
| 5,012,845 | 5/1991 | Averette | 141/329 |
| 5,052,437 | 10/1991 | Danna | 137/587 |
| 5,151,178 | 9/1992 | Nickerson et al. | 210/198.2 |
| 5,167,810 | 12/1992 | Vassarotti et al. | 210/198.2 |
| 5,213,683 | 5/1993 | Mann | 210/198.2 |
| 5,282,973 | 2/1994 | Mann | 210/656 |
| 5,366,621 | 11/1994 | Bidell et al. | 210/198.2 |
| 5,368,276 | 11/1994 | Pfeiffer | 435/69.1 |
| 5,370,146 | 12/1994 | King et al. | 137/8 |
| 5,432,098 | 7/1995 | Wilks | 436/178 |
| 5,445,180 | 8/1995 | Divall | 137/15.06 |
| 5,540,253 | 7/1996 | Junier | 137/240 |
| 5,564,457 | 10/1996 | Beck | 137/15.06 |

FOREIGN PATENT DOCUMENTS

| | | |
|---|---|---|
| 1 409 035 | 10/1975 | United Kingdom . |
| 2 228 063 | 8/1990 | United Kingdom . |
| 2 258 415 | 2/1993 | United Kingdom . |
| 96/10451 | 4/1996 | WIPO . |

*Primary Examiner*—W. L. Walker
*Assistant Examiner*—Marianne S. Ocampo
*Attorney, Agent, or Firm*—Nields, Lemack & Dingman

[57] ABSTRACT

A chromatography column having at least one central slurry valve positioned at either the top cell assembly and/or the bottom cell assembly. The central slurry valves have a pneumatically actuated valve sleeve which can be shifted to create three different flow configurations. One flow configuration allows for the simultaneous cleaning in place of the flow path used to charge the column with chromatography media and the separate processing of fluid through the chromatography media. The other flow configurations permit the reslurrying and removal of chromatography media from the column, and the subsequent repacking of the column with fresh chromatography media without disassembling the column.

6 Claims, 4 Drawing Sheets

CHROMATOGRAPHIC COLUMN AND VALVE WITH MOVABLE VALVE SLEEVE

BACKGROUND OF THE INVENTION

The present invention relates to a chromatography column which can more readily be packed and repacked than has previously been possible.

Frequently it is desirable to separate out one or more useful components from a fluid mixture that contains' other components which may not be useful or are less valuable. To accomplish this it is often necessary or desirable to fractionate such a fluid mixture to separate out the useful or desired components. This can be carried out by using liquid chromatography systems. Liquid chromatography may briefly be described as the fractionation of components of a mixture based on differences in the physical or chemical characteristics of the components. The various liquid chromatographic systems fractionate the components with a fractionation matrix. Some liquid chromatographic matrix systems fractionate the components of a mixture based upon physical parameters such as molecular weight. Still other liquid chromatographic systems will fractionate the components of a mixture based upon chemical criteria such as ionic charge, hydrophobicity, and the presence of certain chemical moieties such as antigenic determinants or lectin-binding sites on the components.

Chromatography systems of various sizes are used in both laboratory analysis operations and in industrial scale production operations in which separation steps such as separating out a fraction from human blood or separating out impurities from a pharmaceutical can be carried out in a large batch process.

The development of chromatography columns has aimed at providing ease of operation and various additional benefits which have particular commercial importance. These include: (a) the ability to be sterilized by autoclaving; (b) improved sanitation by virtue of design features giving less carryover of product from one batch to the next; (c) the ability to resist solvents; (d) material conformity to food grade FDA regulations; (e) an improved pressure tolerance; (f) lower cost; and (g) the potential for full or partial automation.

Traditionally, a chromatography column must be disassembled to reslurry and remove chromatography media in order to repack the chromatography column with fresh chromatography media or with different chromatography media specific for an application. This procedure has several problems. First, the time required to perform this operation is substantial, especially with large industrial columns, and results in lost productivity in a commercial operation. Second, the constant assembly and disassembly of the chromatography column creates excessive wear on the components and leads to a reduced life of the chromatography system. Third, mechanical lifting equipment and significant floor and head space are required. Finally, each time a chromatography column is disassembled there are increased opportunities for unwanted contaminants to be introduced into the column, which can subsequently contaminate the fluid mixture and fraction of interest.

Another problem associated with some types of chromatography columns is the inability to clean the flow path used to introduce chromatography media into the chromatography column while maintaining a barrier between the cleaning solution and the packed chromatography media.

SUMMARY OF THE INVENTION

The problems of the prior art have been solved by the present invention, which provides an engineered column including one or two slurry inlet/outlet valves. In the embodiment employing two valves, one is located at the top of the column and the other spaced from it at the bottom. Each valve has three ports. Port 1 is for feeding slurry into the column during packing and for pumping liquid into the column for reslurrying during unpacking. Port 2 is for expelling "clean" liquid pumped via port 1 to flush out the slurry line after packing, and for removal of reslurried gel during unpacking. Port 3 is the inlet and outlet for the mobile phase, and communicates directly with and only with the distribution cell.

A pneumatically actuated valve sleeve assumes three different positions depending upon the mode of operation. In the bottom valve during packing, the valve sleeve is in the semi-retracted packing position, which closes off port 2 from communication with the inside of the column. When in this position, slurry is pumped into the column via port 1, and air or excess liquid is removed via port 2 of the top valve When the column is purged of air, the valve sleeve of the top valve is in the closed (i.e., fully extended into the housing) position. This directly addresses the failure of the existing art whereby at the cessation of packing, alternative methods suggest the removal of a probe from the column, leaving a void above the closed valve. The present invention prevents the occurrence of this occlusion by improved design. Such a void has a progressively deleterious effect on the chromatographic performance of the column. A further advantage of the present invention is that, by momentarily or constantly maintaining the top valve open to allow passage of fluid from the column via port 2, the column can be very effectively purged of pockets of air which otherwise greatly impair the ability to form homogeneous packed beds.

In the run position, the valve sleeves for both the top and bottom valves are in the unactuated position, closing port 1 and port 2. When in this position, clean liquid can be pumped from port 1 to port 2 to remove any media (gel) left in the slurry line or to carry out a clean-in-place ("CIP") cycle on these lines. The column is then run by pumping mobile phase through port 3 to (and from) the distribution cell.

There are three methods to reslurry a packed bed. In the first method, the bottom valve is in the fill (valve sleeve partly retracted) position and the top valve is in the drain position where the valve sleeve of the top valve is fully retracted from the column housing. When the valve sleeve of the top valve is in this position, clean liquid can be pumped via port 1 through the nozzles at the end of the tube to reslurry the gel, which is then removed through port 2. In the second method, both the bottom and top valves are in the drain position (with the sleeves fully retracted). Clean liquid is pumped into the column via port 1 of either the top or bottom valve to reslurry the gel. Reslurried material passes out through the bottom of the column. In the third method, the top valve is in the fill (sleeve partly retracted) position and the bottom valve is in the drain (sleeve fully retracted) position. This enables slurrying of the top of a packed bed and the slurry passes out of the bottom valve. All three methods can be used in combination during a reslurry operation.

To drain or empty the column, both top and bottom valves are in the drain position and either pump is reversed to withdraw liquid from the column. Alternatively, a combination of pumps may be used to inject and drain the column simultaneously through port 2 on either valve. In addition, slurry may be recycled to the column to greatly reduce the quantity of clean liquid needed to flush the column.

It is therefore an object of the present invention to provide a chromatography column in which the tedious operation of disassembling the column to reslurry and remove chromatography media and repack the column can be avoided by use of a new and useful valve design to permit both the introduction of the chromatographic media into the column and subsequent resuspension and removal after use. This operation can be made fully automated such that for convenience, where space is restricted or certain hazards exist, the column valve can be operated remotely. The pneumatic control circuitry provides a means for affirmative feedback of the valve position and, together with automation, provides the ability to validate specific packing and unpacking methods which may either by generic or specific to the chromatography media and require minimal or no operator intervention.

It is another object of the present invention to enable the flow path used to introduce chromatographic media into the chromatography column to be cleaned in place, while the chromatography column is separating the fluid mixture into the fractions of interest. This solves the problem of the drying out, settling, and eventual hardening of the chromatographic media remaining in the flow path used to introduce the media into the chromatography column. Dried chromatography media is difficult to remove.

Accordingly, the present invention is comprised of a chromatography column including a column tube unit, a fixed cell assembly and an adjustable cell assembly. The column tube unit is bounded on the top or bottom by the adjustable cell assembly, and on the reverse end by the fixed cell assembly. The column tube unit holds the chromatography media once it has been introduced to the column through either the fixed cell assembly or the adjustable cell assembly.

The fixed cell assembly may incorporate the base of the column and the bottom flow distribution cell using the new valve design. The base incorporates levelling screws to enable the column to be accurately levelled, which is essential for efficient chromatography. The bottom flow distribution cell incorporates a minimum dead space fixed sealing arrangement whereby when the fixed cell, bed support, and column tube unit are assembled there are no unswept areas within the process flow path ensuring sanitary performance.

The adjustable cell assembly uses the new valve design and is provided with a range of vertical adjustments to allow the position of the distribution cell to be varied in the column to achieve a range of chromatography media bed heights, and also to permit adjustment of the end cell to take up any voids that may develop during operation of the column. Adjustment of the end cell may be by any suitable means, including manual, hydraulic, electrical or pneumatic, dependent on convenience and whether the chromatographic application benefits from additional compaction. The lower and/or upper cell assembly and bed support may be coned to facilitate draining of liquid or purging of air.

The new valve design used on both the fixed and adjustable cell assemblies permits the reslurrying and removal of used chromatography media and the subsequent introduction of fresh chromatography media without the time and resource-consuming step of disassembling the column. Positioning of the new valve at the top and bottom of the column allows for the process of reslurrying and removal of used chromatography media and the addition of fresh chromatography media to be performed through either the top or bottom of the column depending on each user's unique needs.

BRIEF DESCRIPTION OF THE DRAWINGS

In order that the present invention may more readily be understood the following description is given, merely by way of example, with reference to the accompanying drawings, in which.

DETAILED DESCRIPTION OF THE INVENTION

Figure 1:
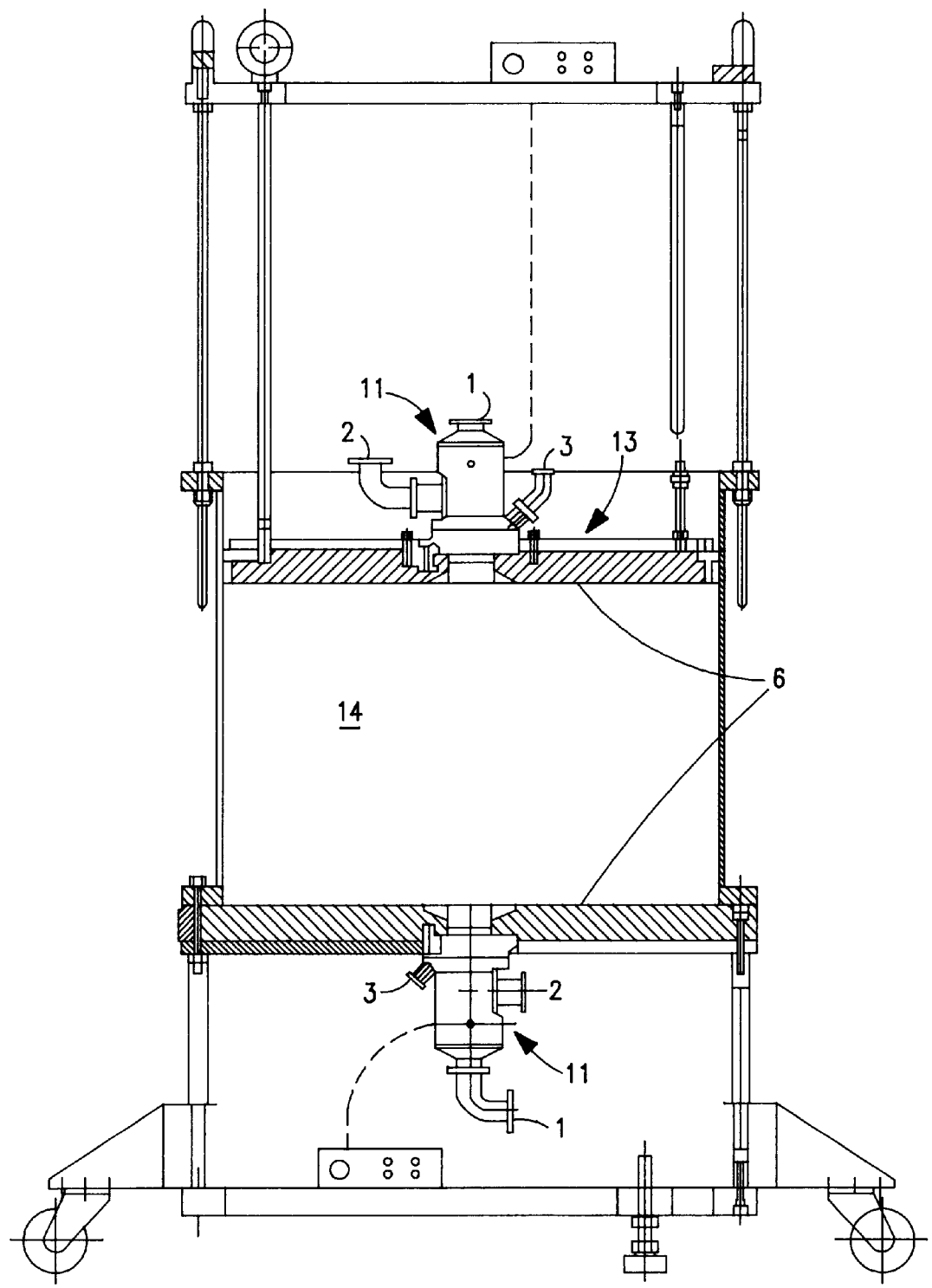
FIG. 1 is a cross section of the chromatography column including the slurry valve constructed in accordance with the present invention.

Referring now to the drawings, FIG. 1 shows the chromatography column fitted with two slurry valves constructed in accordance with the principles of the present invention. In the embodiment shown, the column is comprised of an upper adjustable cell assembly, a hollow cylindrical housing preferably constructed of stainless steel, and a lower fixed cell assembly. Both cell assemblies have slurry valves positioned at the center. The present invention includes within its scope embodiments wherein the adjustable cell assembly is at the bottom of the column, and the fixed cell assembly is at the top.

Figure 2:
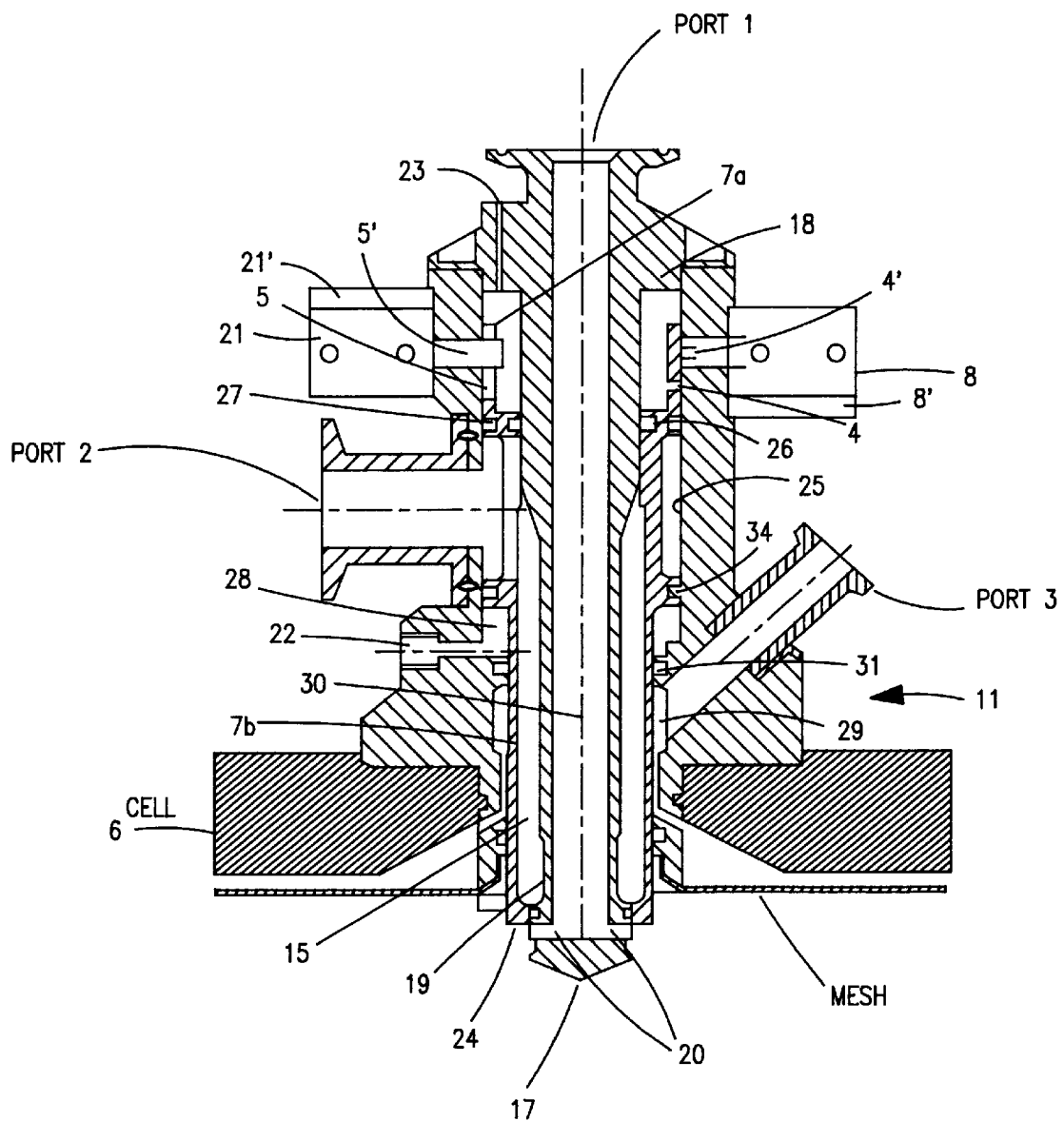
FIG. 2 is a longitudinal cross section of the slurry valve in the packing position.
Figure 3:
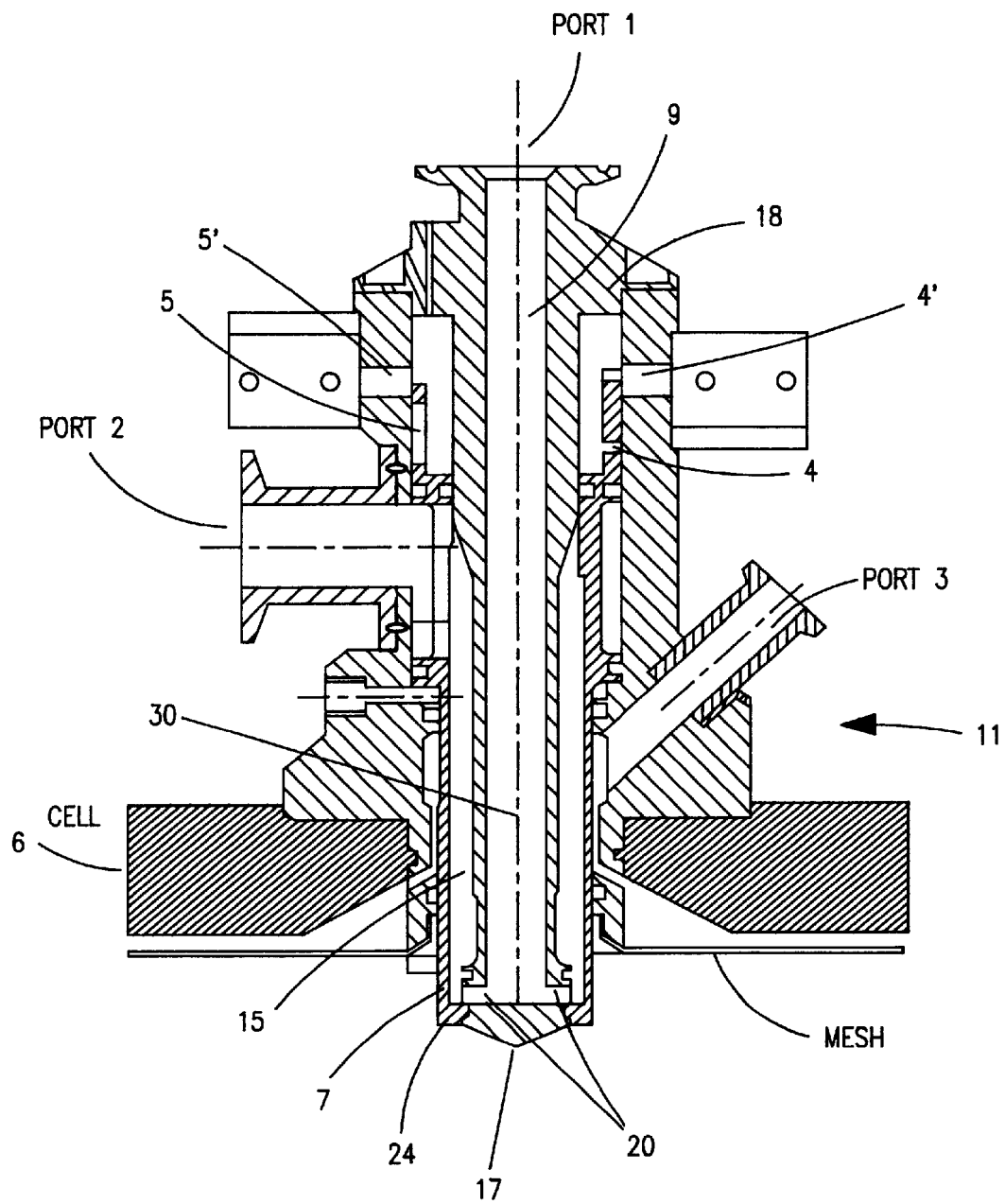
FIG. 3 is a longitudinal cross section of the slurry valve in the running position.
Figure 4:
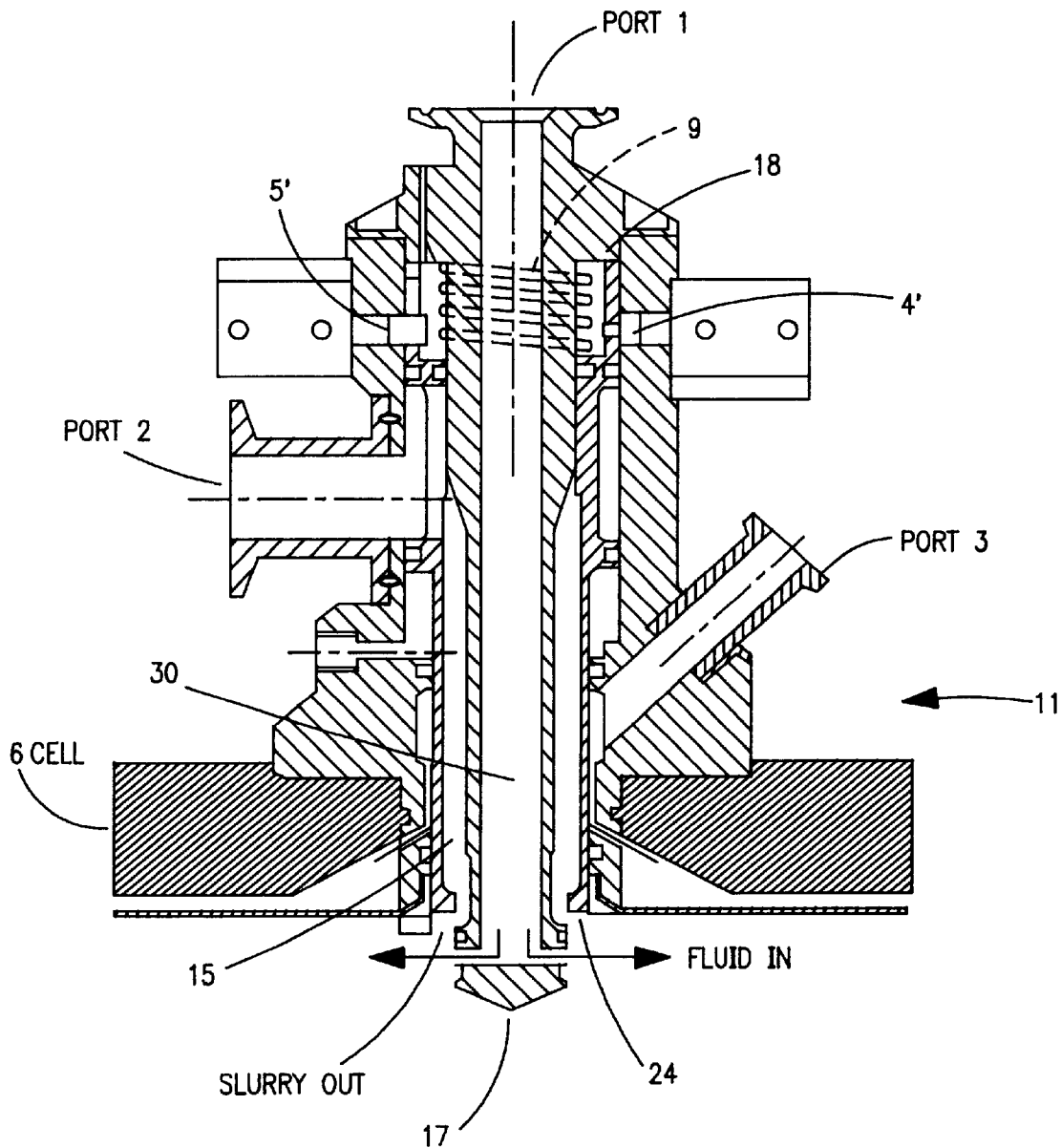
FIG. 4 is a longitudinal cross section of the slurry valve in the unpacking position.

The details of the central slurry inlet/outlet valves 11 may be understood with reference to FIGS. 2, 3 and 4. The valves comprise a housing having a central bore 15 communicating with three ports. A fixed longitudinal member 18 is located in central bore 15 and itself has a central lumen which serves as a slurry feed line 30. The slurry feed line 30 communicates at one end with port 1 and at its opposite end with the interior of the column through radially disposed nozzles 20. The longitudinal member terminates in a domed head 17 that extends into the column at all times. The longitudinal member 18 has an annular portion 19 reduced in diameter to accommodate, in a sealing manner, the valve sleeve 7 as will be discussed in greater detail below. The three ports of each of the valves 11 are used as follows: port 1 for pumping slurry through a slurry feed line 30 into the column, and for pumping liquid into the column for reslurrying during unpacking; port 2 for removal of reslurried gel during unpacking; and port 3 which is the inlet and outlet for the mobile phase, this port communicating directly with, and only with, the distribution cell 6.

Ports 1 and 2 may be closed off from the column by means of an annular valve sleeve 7 slidably positioned in the central bore 15. The valve sleeve 7 includes an upper portion 7a, which is L-shaped in cross-section. The upper portion 7a includes a pin hole 4 and an axial pin slot 5, for receiving pins 4', 5', respectively, in order to lock the valve sleeve 7 in its various positions. The valve sleeve 7 also includes an annular lower portion 7b. The bottom end of the lower portion 7b includes an annular lip 24 adapted to seal against the head 17 in the running position (FIG. 3), and against the longitudinal member 18 in the packing position (FIG. 2). However, the annular lip 24 must be of a diameter small enough so that in the unpacking position (FIG. 4), a gap is created with the annular reduced diameter portion 19 of the longitudinal member, so as to allow communication between the central bore 15 and the column interior. The valve sleeve 7 may be actuated by any suitable means, such as manually, or electrically, or hydraulically, or preferably pneumatically.

In the present embodiment the sleeve 7 is driven axially by application of compressed air through either of two pneumatic ports 22 and 23.

In particular, the sleeve 7 has an outwardly extending land 34 slidable within a cylindrical wall portion 25 of the valve body, and an inwardly extending land 26 and an outwardly extending land 27 at the same axial positions just above the port 2, such that the outwardly extending land 27 slides along the same cylindrical wall portion 25 of the valve body and the inwardly extending land 26 slides along a cylindrical exterior of an upper part of the longitudinal member 18 of the valve.

Below the land 34 of the sleeve 7, the valve housing has an inwardly extending land 31 which will be fixed in position and which, together with the land 34 on the moving valve sleeve 7, defines a fluid pressure chamber portion 28 of the central bore, isolated from another chamber portion 29 into which the third port 3 opens and which communicates with the distribution cell 6.

The inner pneumatic port 22 thus provides a means of applying pressure to the chamber portion 28 below the land 34 for the purposes of retracting the sleeve 7 (moving it relatively upwardly in FIG. 2). Similarly application of compressed air to the outer pneumatic port 23 applies pressure above the twin lands 26 and 27 and drives the sleeve 7 axially inwardly (downwardly in FIG. 2). In this manner the axial movement of the sleeve can be effected.

However, this pneumatically activated axial movement of the sleeve 7 is required to cause it to occupy one of three different positions and these positions are defined by virtue of the pins 4', 5' which co-operate with the hole 4 and the axial slot 5 of the valve sleeve.

FIG. 2 shows the "packing" position in which slurry can be discharged from the head 17 of the fixed longitudinal member 18 by virtue of retraction of the sleeve 7 (upwardly in FIG. 2) so that it just exposes the nozzles 20 of the head 17 but still seals against the exterior of the head. In this position the pin 4' must be retracted and the pin 5' is extended to engage in the outer end (top in FIG. 2) of the slot 5 of the valve sleeve. By positively checking that the pin 4' driven by the actuator 8 is retracted and that the pin 5' driven by the actuator 21 is extended there is achieved a feedback which confirms that the sleeve is in the "packing" position. This positioning of the pins 4' and 5' in the actuators 8 and 21 is checked by virtue of reed switches 8' and 21' of the respective actuators.

When the valve sleeve 7 is to be retracted to the FIG. 3 "running" position for the purposes of leaving valve port 3 open to the media in the bed by way of the filter mesh of the distribution cell 6, the pin 5' must be retracted in order to allow the sleeve 7 to pass downwardly in FIG. 3 far enough to bring the slot 5 no longer in register with the pin 5'. The pin 4' is then driven by the actuator 8 to extend above the upper rim of the valve sleeve 7 to hold it firmly in the "Running" (FIG. 2) position. This time the positive feedback checking of the position of the valve is derived by checking that the pin 5' is retracted and pin 4' is extended, again using the reed switches 8' and 21'.

When finally the valve sleeve is to be fully retracted to the "unpacking" position shown in FIG. 4 it moves through the FIG. 2 position. This time it reaches a fully raised position as viewed in FIG. 4 where the pin 5' can again engage in the slot 5 and the pin 4' can now engage in its hole 4 so that the positive feedback checking action by the reed switches 8' and 21' checks that the two pins 4' and 5' are advanced.

If the pneumatic control system energising the actuators 8 and 21 fails to detect that the pin 4' is advanced when the "unpacking" (FIG. 4) position has been selected then there will be a malfunction indicated to show that the valve is not fully open. Likewise, if in the FIG. 2 position the pin 5' is not confirmed as being fully extended then again a malfunction will be indicated to show that the sleeve has descended too far and beyond the "packing" (FIG. 2) position.

The valve is thus positively driven upwardly and downwardly and the location of it in each of its three positions is clearly defined by the pins 4' and 5' driven by the actuators 8 and 21 and checked by the reed switches 8' and 21' of those actuators.

Additionally the valve member may be biased axially (in this case downwardly as viewed in FIG. 4) by an optional helical compression spring 9 around the fixed longitudinal member 18 and pressing downwardly against the inwardly directed land 26 of the valve sleeve. Thus the default position, when the air supply (not shown) is disconnected from the pneumatic control circuit after packing or for storage, is the "Running" FIG. 3 position, closing ports 1 and 2 off from the column. This occurs when the air pressure at pneumatic port 23, and optionally the force of spring 9, forces the valve sleeve 7 to the closed position (FIG. 3). As indicated above, the valve sleeve 7 is held in closed position both by the axial forces and the locking pin 4' of the pneumatic actuator 8 being extended above the top of the sleeve. This prevents the sleeve 7 from opening inadvertently or due to operating pressure in the column. Those skilled in the art will understand that the description of a pneumatically actuated valve sleeve is for illustrative purposes only; the claims set forth below are intended to encompass any means for actuating the valve operation, including both automated, electrical pneumatic valve opening and/or closing, as well as manually actuated adjustments to the positioning of the valve sleeve 7.

The pneumatic control circuit to operate the actuators 8 and 21 will be readily apparent to the man skilled in the art and is not described herein in detail.

One typical operation of the inlet/outlet slurry valves 11 is as follows. Starting from the unpacking position shown in FIG. 4, hydraulic pressure is applied to the outer pneumatic port 23 and the actuator 8 is operated to retract the pin 4' from its hole 4 to allow the sleeve to move inwardly (down in FIG. 4). This movement is arrested once the outer (top in FIG. 4) end of the axial slot 5 abuts the still extended pin 5' held by the actuator 21. In this position, the valve sleeve 7 closes port 2 by creating a seal between the annular lip 24 of lower potion 7b of valve sleeve 7 and the longitudinal member 18, thereby closing central bore 15 from the column interior.

to place the upper slurry valve 11 in the "running" position (as shown in FIG. 3) requires the actuator 21 to withdraw the pin 5' from the slot 5, allowing the pneumatic pressure on the outer pneumatic port 23 to drive the sleeve still further forwardly until the FIG. 3 position is attained. At this point the actuator 8 is then operated to advance the pin 4' so it sits just above the axially outer rim of the valve sleeve 7 and holds the sleeve against retraction from the FIG. 3 position.

In this position, the annular lip 24 seals against the head 17, thus closing ports 1 and 2. Slurry is fed, for example by a pump, through port 1 of the bottom slurry valve 11 and the slurry feed line 30 into the column. The chromatography media is retained in the column by the distribution cell 6 of the adjustable cell assembly 13, while air and the liquid forming the slurry with the chromatography media are removed, initially venting through port 2 of upper slurry valve 11 until the column is purged of air, and subsequently through port 3 of the upper slurry valve 11.

When the packing of the column with chromatography media 14 is complete, the pneumatic control circuit places the valve sleeve 7 of the lower slurry valve 11 into the closed/running position (FIG. 3) in the manner just described for the upper valve 11, thus closing off ports 1 and 2 from the column. This creates a flow path through slurry feed line 30 and central bore 15 from port 1 to port 2, through which a cleaning solution can be fed, for example by a pump, to clean in place port 1, port 2, and the slurry feed line 30. This cleaning operation can be performed at the same time as the processing of the liquid to be separated to prevent the settling and hardening of any residual chromatography media 14 in the slurry feed line 30. This operation of cleaning can be made to automatically follow setting the slurry value to closed/running for operator convenience.

The chromatography column is now ready to separate the mixture of interest. The mixture (mobile phase) to be separated is fed, for example by a pump (not shown), through port 3 of either the upper or bottom slurry valve 11 into the column through the distribution cell 6 and then flows through the chromatography media 14 and is removed through port 3 of the other slurry valve 11.

After the mixture of interest has been separated, or if for any other reason, it becomes necessary or desirable to reslurry and remove the chromatography media 14, the upper slurry valve 11 and the bottom slurry valve 11 are placed in the unpacking position (FIG. 4), where both pins 4' and 5' are engaged in pin holes 4 and 5, respectively. This causes the bottom portion 7b of the valve sleeve to be fully retracted, allowing communication between the column interior and the central bore 15. This unpacking position is achieved from the running position by firstly operating the actuator 8 to retract the pin 4' from the hole 4, and then applying pressure to the inner pneumatic port 22 to retract the valve sleeve 7 (and in so doing overcome the spring force of the optional spring 9) until the end position of travel is reached where the sleeve 7 is fully retracted. At this point the actuators 8 and 21 can both operate to advance their respective pins 4' and 5' into the hole 4 and axial slot 5, respectively, of the sleeve. Only when these two pins have been advanced is there attainment of the positive feedback signal from the reed switches 8' and 21'.

Clean liquid is initially introduced into the column (such as by a pump) via port 1 of the bottom slurry valve 11, which reslurries the chromatography media 14 which is removed through port 2 of the bottom slurry valve. Removal of chromatography media slurry by port 2 may be assisted by a second pump (not shown) in which case the upper slurry valve 11 is placed in the unpacking position. The clean liquid is then switched to be introduced via port 1 of the top valve. The effect is to wash out a core of packed chromatography media from near the top valve and from near the bottom valve. An additional but optional method of unpacking is the backflush through the filter mesh of the lower distribution cell 6 to fluidize the media (gel) to assist draining of slurry from the column.

After a short period the dilute slurry washed from the column can be recycled to the port 1 of the top valve in place of clean liquid, thereby reducing the quantity of clean liquid required.

Clean liquid or a sanitizing agent may be used for the final flushing of the column. The use of a slurry valve 11 on both the upper and bottom cell assemblies facilitates the loading and removal of chromatography media 14 through either the top or bottom of the column. Another benefit of using a slurry valve 11 on both the upper and bottom cell assemblies is the ability to flow the mixture to be separated in either a top-to-bottom, or bottom-to-top flow path. By judicial use of slurry or fresh buffer, it is possible to minimize the volume of liquid needed to re-slurry the contents of the column and empty the column of gel. It is understood that the use of two valves in the preferred embodiment is meant for the purposes of illustrating many of the versatile uses of the valve, and is not meant as a limitation. Those skilled in the art will realize that it is possible to use only one slurry valve, on either the upper or bottom cell assembly, although the performance options would be more limiting. All such modifications which do not depart from the spirit of the invention are intended to be included within the scope of the appended claims.

Particular regard has been made to the cleanability of the valve. Sanitary design has been applied to the type of hose couplings, material selection and finish, sealing technology and method for cleaning in place (CIP). The valve may be cleaned in place when in the running position (FIG. 3), leaving no unswept surfaces. The profile, location, number and material used for the seals is particularly important. Suitable materials include EPDM, PTFE or composite materials for the seal material.

Once the internal passages through ports 2 and 1 have been cleaned in place, the valve can either be blown through with air or left full with fluid, and all connections for pneumatic actuation and slurry process lines can be disconnected. This enables the column to either be stored or operated in the running FIG. 3 position, without attachment to a station for transferring slurry to or from the column.

The pneumatic control circuit provides positive locking positions for each of the three positions of the valve sleeve 7 and positive feedback confirmation of those positions. By use of positional indicators on the pneumatic control circuit, it is possible to provide affirmative feedback of the sleeve position to provide operator validation information. Two indicators are used for this in the preferred embodiment, but more or less can be used as will be readily appreciated by those skilled in the art.

What is claimed is:

1. A chromatography column, comprising:

an elongated column tube having a first end and a second end spaced from said first end;

first valve means associated with said first end;

second valve means associated with said second end;

wherein at least one of said first and second valve means has a central bore comprising a fixed longitudinal member disposed in said central bore, said longitudinal member having a passageway communicating with said column tube; a first port communicating with said passageway for feeding slurry into said column during packing of media; a second port communicating with said central bore for liquid to flush out said valve means; a third port communicating with said central bore but isolated from said passageway and said second port for the supply and removal of liquid to be separated by said media in said column; and a valve sleeve disposed in said central bore and moveable with respect to said longitudinal member between a first position allowing communication between said first port and said column through said passageway while precluding communication between said second port and said column, a second position precluding communication between said first port and said column and between said second port and said column, and a third position allowing communication between said first port and said column and between said second port and said column.

2. The chromatography column of claim 1, wherein said longitudinal member terminates at one end in a head disposed in said column.

3. The chromatography column of claim 2, wherein said valve sleeve seals against said head when in said second position.

4. The chromatography column of claim 1, wherein said valve sleeve is pneumatically actuated for movement between said first, second and third positions.

5. The chromatography column of claim 1, wherein said longitudinal member comprises a portion reduced in diameter, and wherein said valve sleeve terminates in an annular lip, the dimensions of said annular lip being such that a gap is formed between said annular lip and said portion reduced in diameter when said valve sleeve is in said third position.

6. The chromatography column of claim 1, wherein said valve sleeve envelops said longitudinal member.

* * * * *